United States Patent

Aronow

[11] Patent Number: 6,018,674
[45] Date of Patent: Jan. 25, 2000

[54] FAST-TURNOFF PHOTODIODES WITH SWITCHED-GAIN PREAMPLIFIERS IN PHOTOPLETHYSMOGRAPHIC MEASUREMENT INSTRUMENTS

[75] Inventor: Kurt Albert Aronow, Lafayette, Colo.

[73] Assignee: Datex-Ohmeda, Inc., Liberty Corner, N.J.

[21] Appl. No.: 08/908,101

[22] Filed: Aug. 11, 1997

[51] Int. Cl.[7] .................................................. A61B 5/00
[52] U.S. Cl. ........................................... 600/322; 600/323
[58] Field of Search .................................. 600/310, 322, 600/323, 326, 330, 331, 336; 356/39, 41

[56] References Cited

U.S. PATENT DOCUMENTS

| | | | |
|---|---|---|---|
| 4,819,752 | 4/1989 | Zelin | 600/323 |
| 4,942,877 | 7/1990 | Sakai et al. | 600/323 |
| 5,078,136 | 1/1992 | Stone et al. | 600/323 |
| 5,766,127 | 6/1998 | Pologe et al. | 600/323 |

*Primary Examiner*—Eric F. Winakur
*Attorney, Agent, or Firm*—Holme Roberts & Owen LLP

[57] ABSTRACT

An improved photoplethysmographic measurement system is disclosed in which a fast-turn-off photodiode is used in order to minimize the effect of "bleed-through" voltages on the dark time (ambient) light determination. Particularly in photoplethysmographic instruments which utilize switched-gain preamplifiers the "bleed-through" of voltage which should be associated with the excitation of the photodiode by the emitter into the dark time or ambient light calculation will negatively impact the accuracy of blood analyte determination. A hardware method and a software method for determining whether a given photodiode has a sufficient decay time are also disclosed.

7 Claims, 9 Drawing Sheets

FAST-TURNOFF PHOTODIODES WITH SWITCHED-GAIN PREAMPLIFIERS IN PHOTOPLETHYSMOGRAPHIC MEASUREMENT INSTRUMENTS

FIELD OF THE INVENTION

This invention relates to systems that utilize photodiode detectors and, more particularly, to an improved photoplethysmographic measurement instrument in which a fast-turnoff photodiode detector is used in conjunction with a switched-gain preamplifier.

BACKGROUND OF THE INVENTION

Photoplethysmographic measurement instruments are configured to emit light of at least two different, predetermined wavelengths through a selected portion of a patient's anatomy (e.g., a finger tip. ear, nasal septum). The analytes to be identified within the patient's blood must each have unique light absorbency characteristics for at least two of the emitted wavelengths. By measuring changes in intensity of the transmitted (the light exiting an absorber is referred to as transmitted) light from the patient's finger (or other suitable area of anatomy) at these wavelengths, each analyte such as reduced hemoglobin (RHb) and oxygenated hemoglobin ($O_2Hb$) may be determined. Thereafter, characteristics such as blood oxygen saturation ($SpO_2$) may be determined based on these analytes. An example of this type of photoplethysmographic instrument which measures reduced hemoglobin (RHb) and oxygenated hemoglobin ($O_2Hb$), known as a pulse oxinmeter, can be found in U.S. Pat. No. 5,503,148 to Pologe et. al which is incorporated herein by reference.

Photoplethysmographic monitors have also been developed which use LED's or laser diodes to measure one or more additional blood analytes levels, such as carboxyhemoglobin and methemoglobin, in addition to RHb and 02Hb, based on similar principles to pulse oximetry described above.

Other characteristics such as pulse rate may also be determined based on certain components of the transmitted light signal which passes through the patient's anatomy. Specifically, the transmitted light includes a large DC component and a smaller AC or pulsatile component. By using the pulsatile component, the patients pulse rate may be determined, since fluctuations in the pulsatile component are a function of arterioles pulsating with the patient's heart rate.

In one photoplethysmographic measurement system known as a pulse oximeter, at least two wavelengths of light may be emitted during dedicated, alternating intervals. The transmitted light from the selected body portion is detected by a light-sensitive element such as a photodiode. The photodiode then outputs a time division multiplexed (TDM) signal that includes portions corresponding with each wavelength of the transmitted light For example in a TDM pulse oximeter, each emitted light level can be immediately preceded by an ambient light interval which may also be referred to as a "dark time" interval. The system first de-multiplexes the TDM signal into parallel channels. Signal processing then proceeds wherein a first series of steps performs preliminary filtering. Immediately following the first series of steps, the parallel channels are re-multiplexed. Next, a second series of steps is performed in which the re-multiplexed signal facilitates subtraction of the dark time signal from the signal corresponding with each emitted light interval in a manner known in the art. Such subtraction process may rely on a dark time interval immediately preceding each emitted light interval or at least one of the light intervals in a TDM format. Following the second series of steps, in which ambient light subtraction is accomplished, the TDM signal is de-multiplexed a second time into parallel channels prior to the completion of signal processing.

The photodiodes used as the light sensitive elements in pulse oximeters do not turn off instantaneously after the excitation of the emitters, and, therefore the transmitted light incident on the photodiode, ceases. In other words, the received light signal coming from the photodiode as a result of the emitted light being transmitted through the tissue of the patient may take more than 100 microseconds to decay from 10% to 0.1% of the maximum received light signal intensity. This compares to a decay time of perhaps only several microseconds for the decay from 90% to 10% of the maximum received light signal intensity. This slow turn-off of photodiodes for the last 10% of decay can erroneously become a portion of the integrated ambient light level of the following channel. Because the light level used for calculations for any channel is simply the difference between the channel's light time and dark time, an error in the dark time is essentially the same as an error in that channel's light time.

The problems associated with the slow turn-off of photodiodes are also exacerbated at longer wavelengths and when a large gain disparity exists between the two channels (e.g., the gain is greater for the second channel). As the gain disparity increases so does the error caused by the undecayed signal which bleeds through the photodiode into the ambient light measurement.

SUMMARY OF THE INVENTION

Accordingly, the primary objective of the present invention is to provide an improved photoplethysmographic measurement system wherein the effect of the decay time of the photodiode on the magnitude of the ambient light subtracted from a TDM signal being sent from the sensor to the photoplethysmographic monitor is minimized.

In order to achieve such objectives, a system is provided wherein the photodiode has an appropriate decay time for use in a photoplethysmographic system.

In a primary embodiment of the invention, a photoplethysmographic measurement system includes means for emitting light having spectral contents characterized by certain predetermined center wavelengths. The emitted light is transmitted through a portion of a patient's anatomy. The transmitted portions of the emitted light for each center wavelength and the ambient light level are detected by a photodiode so as to form respective ambient and detected light signal portions within the TDM signal. The photodiode is selected so that the decay time of the photodiode minimizes the effect of the "bleed-through" or residual voltage TDM signal. The problem of "bleed-through" from one TDM channel to the next exists in standard pulse oximetry which uses two emitters having spectral contents characterized by center wavelengths in the red and infrared bands, as well as for photoplethysmographic systems having more than two emitters.

First and second amplification means are provided, each of which includes a first input, a second input and an output for producing an amplified output. The output produced by each amplification means is proportional to a difference between signals present on its first and second inputs multiplied by a predetermined and variable gain, i.e., switched gain amplification. The outputs from the amplification means are then processed to determine certain characteristics including, but not limited to, a patient's pulse rate and blood oxygen saturation level and/or specific blood analyte information such as, for example, the concentration (as a percentage of total hemoglobin) of oxyhemoglobin ($O_2Hb$), deoxyhemoglobin (RHb), carboxyhemoglobin (COHb) or methemoglobin (MetHb) or to otherwise provide an indication when one of such measures exceeds a predetermined level of interest.

The concentrations of a plurality of the noted analytes of interest may be determined by using at least a common plurality of emitted wavelengths, provided that the analytes exhibit unique absorbence behavior at the emitted light wavelengths. By measuring changes in intensity of the transmitted light, for example, from a finger at the emitted wavelengths and based on the corresponding outputs of the amplification means, the aforementioned analytes are among those which may be determined in processing. Thereafter, characteristics such as blood oxygen saturation may be determined based on these analytes. Other characteristics such as pulse rate may be determined based on certain components of the transmitted light signal which passes through the patient's anatomy. Specifically, the transmitted light includes a large DC component and a smaller AC or pulsatile component By using the pulsatile component, the patient's pulse rate may be determined, since fluctuations in the pulsatile component are a function of arterioles pulsating with the patient's heart rate.

Methods for determining the decay time of various photodiodes is also described as an integral part of manufacturing the photoplethysmographic monitors of the present invention. The photodiodes which minimize the effect of "bleed-through" voltage on the next channel's ambient light (dark time) signal can be identified either through the use of a hardware test fixture or a software routine which can be implemented in a standard photoplethysmographic monitor test which uses switched gain amplification.

The present invention enables more accurate pulse oximeters and other photoplethysmographic monitors to be developed. As the number of blood analytes being measured increases and as the center wavelengths of the emitted light used to measure these additional blood analytes changes, it is important to increase the accuracy of the photoplethysmographic instruments as much as possible.

BRIEF DESCRIPTION OF THE DRAWINGS

For a more complete understanding of the present invention and further advantages thereof, reference is now made to the following Detailed Description, taken in conjunction with the Drawings, in which.

DETAILED DESCRIPTION OF THE INVENTION

Figure 1:
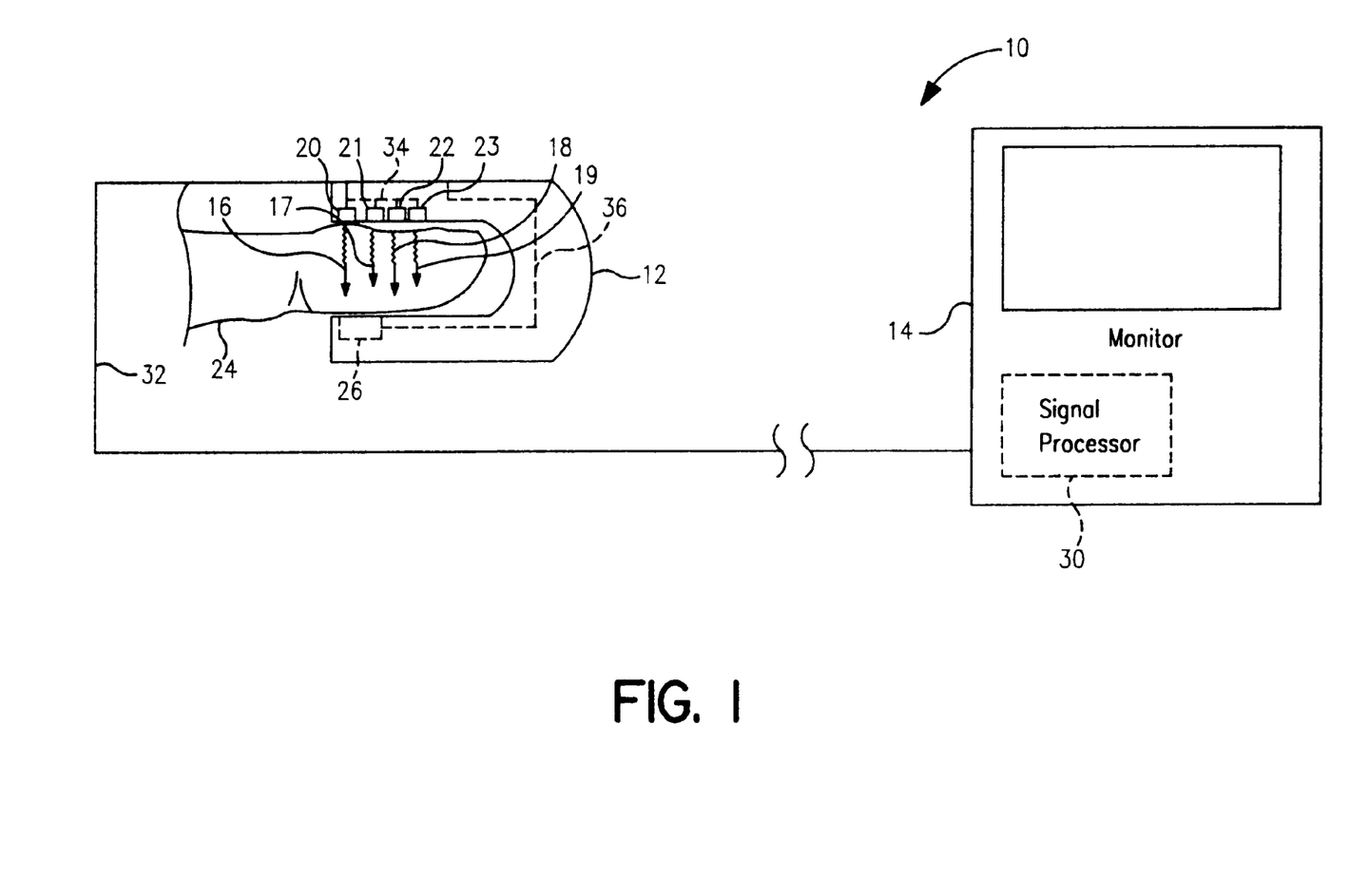
FIG. 1 is a diagrammatic illustration of a photoplethysmographic measurement system implementing the present invention.

FIG. 1 is a diagrammatic illustration of a photoplethysmographic measurement system embodiment, generally indicated by reference numeral 10, constructed in accordance with the present invention. As will be described, the embodiment utilizes a time division multiplexed (TDM) signal in conjunction with an instrumentation-type switched gain amplifier. The system is configured to minimize the effect of the residual voltage which occurs due to the decay time of the photodiode.

System 10 includes a sensor probe 12 and a signal processing assembly in monitor portion 14. Probe 12 contains four emitters 20, 21, 22 and 23 configured for emitting a first light beam 16 having a spectral content centered about a first wavelength ($\lambda_2$),, a second light beam 17 having a spectral content centered about a second wavelength ($\lambda_2$), a third light beam 18 having a spectral content centered about a third wavelength ($\lambda_3$), and a fourth light beam 19 having a spectral content centered about a fourth wavelength ($\lambda_4$). Light having spectral contents characterized by the four wavelengths is sequentially emitted at regular intervals from the four emitters 20, 21, 22 and 23, respectively, which may, for example, comprise light emitting diodes ("LED's") or laser diodes. It should be appreciated that the present invention can be employed in systems utilizing light having spectral contents with fewer, as well as more, than two center wavelengths. The light may be emitted by emitters in the sensor 12 portion of the system or by emitters which are located in the monitor portion 14 of the system where the emitted light is transmitted via optical fiber or another type of light guide to the tissue of the patient.

Continuing to refer to FIG. 1, a portion of the light is transmitted through a portion of a patient's anatomy, such as a finger 24, and is detected by a light-sensitive photodiode 26. Other areas of the patient's anatomy, such as the ear or nasal septum, may also be used provided that the transmitted light suitably passes through such areas. In this regard, the output indications provided by system 10 pertain to arterial blood flow data. More particularly, based upon the absorption of light at the emitted wavelengths certain characteristics may be determined including, but not limited to, a patient's pulse rate and blood oxygen saturation level, including the concentration (as a percentage of total hemoglobin) of oxyhemoglobin ($O_2Hb$), deoxyhemoglobin or reduced hemoglobin (RHb), carboxyhemoglobin (COHb) or methemoglobin (MetHb).

Sensor probe 12 is electrically connected to the signal processor 30 via multi-conductor cable 32. A first set 34 of conductors within cable 32 carries drive signals to light emitters 20, 21, 22 and 23, while a second set 36 of conductors connects to photodiode 26 and to carry a TDM signal to the signal processor 30 within the monitor portion 14 of the photoplethysmographic instrument 10.

Figure 1B:
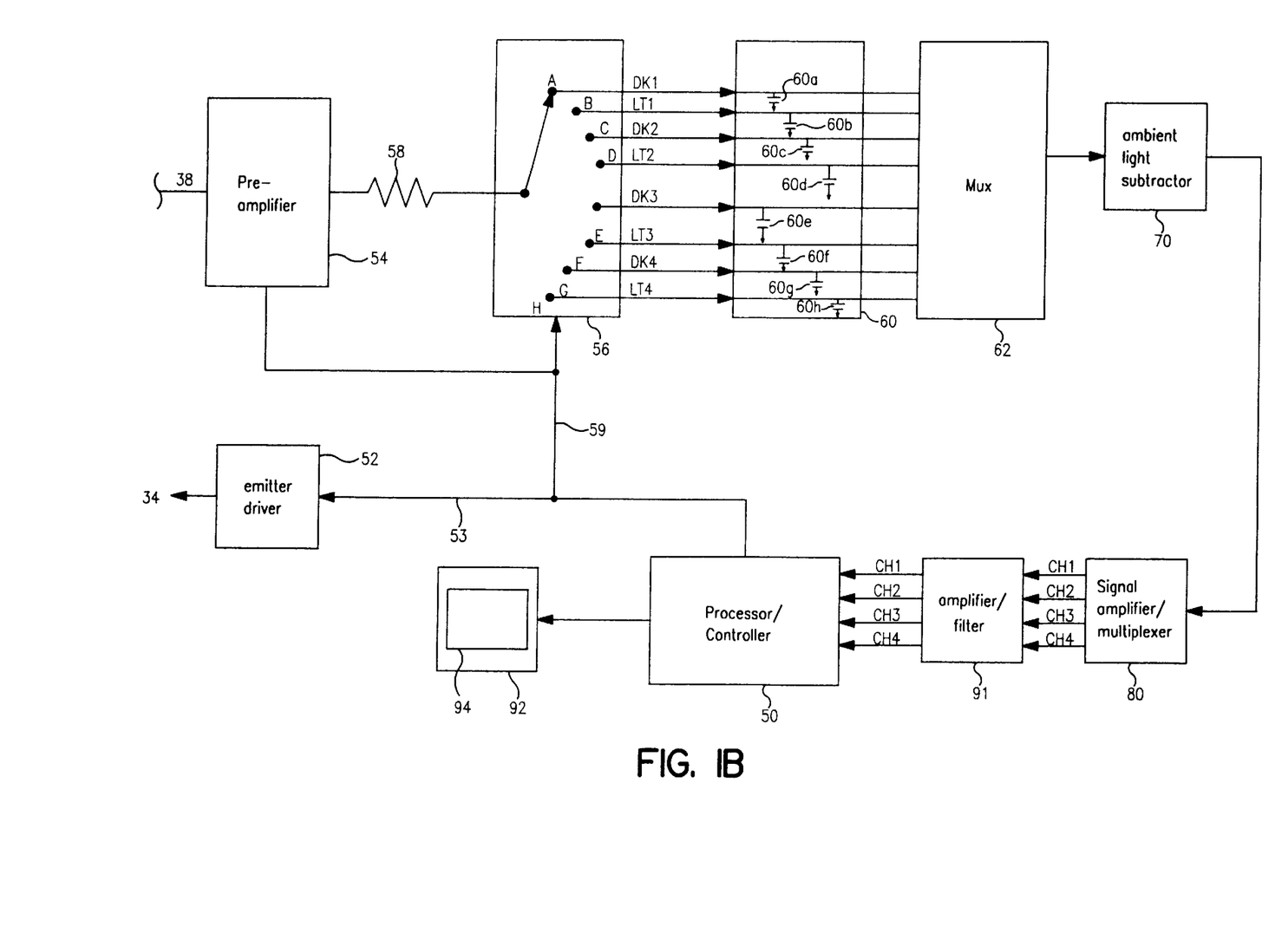
FIG. 1b is a diagram illustrating the processing component of the photoplethysmographic measurement system of FIG. 1.

Referring to FIGS. 1b in conjunction with FIG. 1 the signal processor 30 of monitor portion 14 will now be described. A processing/control section 50 is included which provides drive signals to an emitter driver section 52 through control signal lines 53. The emitter driver section may be configured, for example, to drive LEDs, laser diodes or other such suitable light sources which may become available. The emitter driver section 52 provides drive signal waveforms to probe 12 so as to excite emitters 20, 21, 22 and 23 to emit light beam 16 (of the first wavelength, $\lambda_1$), light beam 17 (of the second wavelength, $\lambda_2$), light beam 18 (of the third wavelength, $\lambda_3$), and light beam 19 (of the fourth wavelength, $\lambda_4$). In turn, photodiode 26 detects the light passing through the selected body portion to output the TDM signal 38 of FIG. 1b.

TDM signal 38 is coupled to a preamplifier 54 via conductors 36 from probe 12. Preamplifier 54 converts the relatively small magnitude current of TDM signal 38 to a voltage level more useful for processing. A silicon switch 56 is connected to preamplifier 54 through resistor 58 (e.g., a 2.1K Ohm resistor). In the present example, silicon switch 56 comprises a single pole, eight-way throw switch which is controlled by processing section 50 by means of control lines 59. Synchronous control of switch 56 is coordinated by processing section 50 with drive signals provided to light source driver section 52 such that TDM signal 38 is de-multiplexed. Specifically, silicon switch 56 outputs eight data channels A, B, C, D, E, F, G and H wherein channel A comprises the DK1 signal portion, channel B comprises the LT1 signal portion, channel C comprises the DK2 signal portion, channel D comprises the LT2 signal portion, channel E comprises the DK3 signal portion, channel F comprises the LT3, channel G comprises the DK4 and channel H comprises the LT4 signal portion.

Following de-multiplexing, the signal on each channel, A–H, charges one of eight holding capacitors 60a –h (e.g., 1.0 $\mu$ F capacitors). These holding capacitors are configured with resistor 58 to form part of a sample and hold circuit (as well as a low-pass filter) in which an average value of each channel over several cycles is stored. In accordance with the present invention, the sample and hold/low pass circuit comprised of resistor 58, capacitors 60 and silicon switch 56 apply the integrated signals LT1', DK1', LT2', DK2', LT3', DK3', LT4', DK4' to a multiplexer 62 regenerating a composite signal then to an ambient light subtractor 70. After ambient light subtraction the signal is amplified and demultiplexed via composite signal amplifier/multiplexer 80. The demultiplexed signal is then filtered further in an amplification/filtering section 91 and is then sent to processing control section 50.

Following processing, i.e., calculation of the blood analyte levels, etc., data is provided by processing/control section 50 to a display 92 including a display screen 94 of a suitable configuration including, for example, LCD and CRT types. Information and related warnings are provided in conjunction with or as an alternative to visual display. For example, in the event that the determined value of a monitored characteristic falls above and/or below predetermined threshold values an audio alarm may sound to alert attending medical personnel.

Figure 1C:
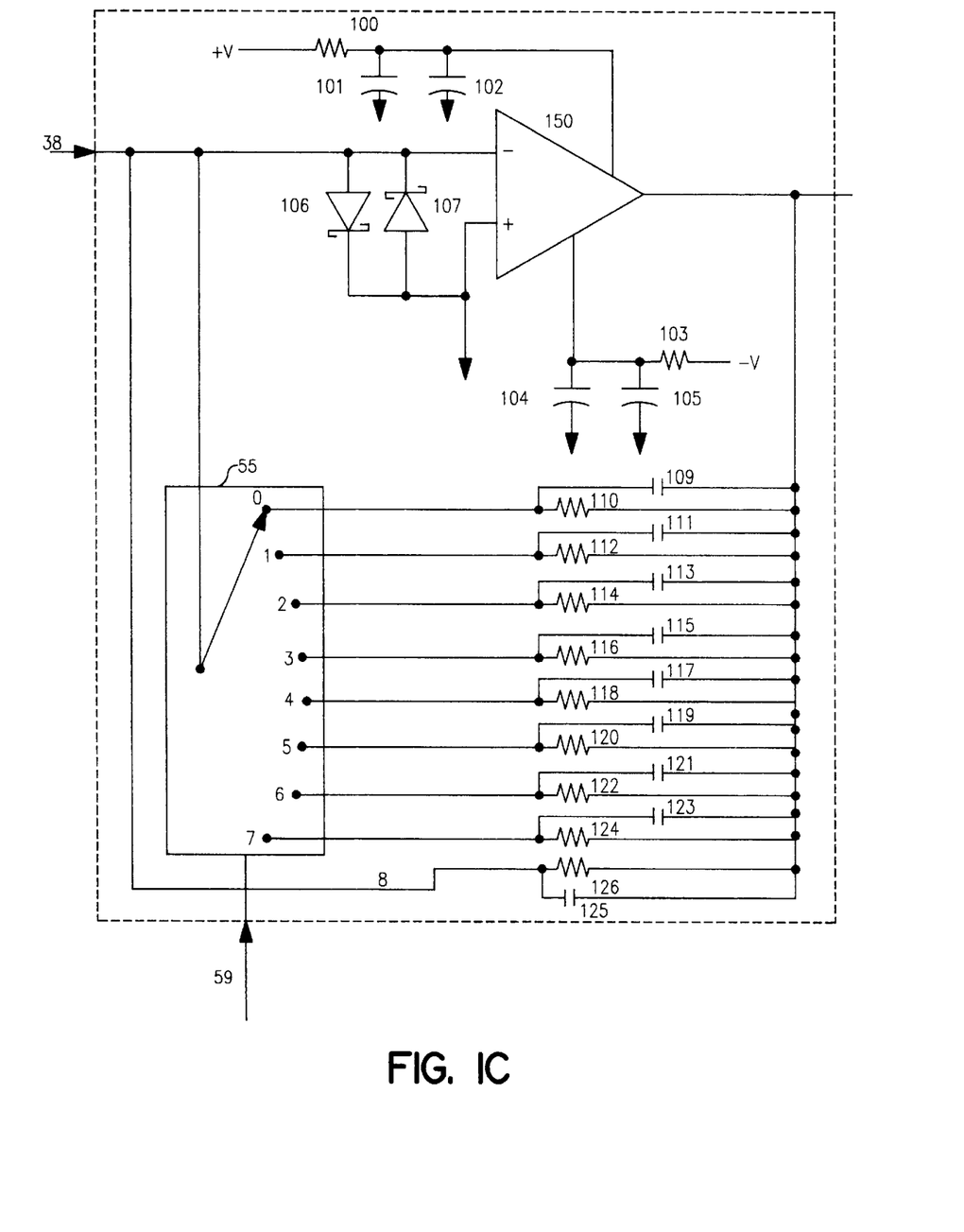
FIG. 1c is a diagram illustrating the pre-amplification component of FIG. 1b.

Reference in now made to control of pre-amplification section 54 shown in detail in FIG. 1c. Control lines 59 connect processing/control section 50 with pre-amplification section 54. The gain, G, of each the pre-amplifier section 54 is connected to processing/control lines 59 as input to an eight-way silicon switch 55 which enables the processing control section 50 to select one of eight gain selections 0, 1, 2, 3, 4, 5, 6, 7, and 8 for the preamplifier which result in the gains set forth in Table 1 below.

TABLE 1

| GAIN SELECTION | GAIN (K Ohm) |
| --- | --- |
| 0 | 9.93 |
| 1 | 18.5 |
| 2 | 34.8 |
| 3 | 63.5 |
| 4 | 119 |
| 5 | 220 |
| 6 | 408 |
| 7 | 757 |
| 8 | 1.4 M Ohm |

In a preferred embodiment of the invention the switched gain preamplifier is comprised of operational amplifier 150, Zener diodes 106, 107, resistors 100 and 103 (49.9 Ohm), decoupling capacitors 101 and 105 (100 $\mu$F) and decoupling capacitors 102 and 104 (0.1 $\mu$F) for filtering the power supply voltages $V_+$ and $V_{31}$ applied to the operational amplifier 150.

The switchable gain section of the preamplifier is comprised of resistors 110, 112, 114, 116, 118, 120, 122, 124 and 126 (preferably having resistive values 10.0 K, 18.7 K, 35.7 K 66.5 K, 130 K, 261 K, 576 K, 1.65 M and 1.4 M Ohm, respectively) and capacitors 109, 111, 113, 115, 117, 119, 121, 123 and 125 (preferably having capacitance values of 1000 pF, 470 pF, 270 pF, 150 pF, 82 pF,39 pF, 18 pF, 6.8 pF and 6.8 pF, respectively).

Figure 2:
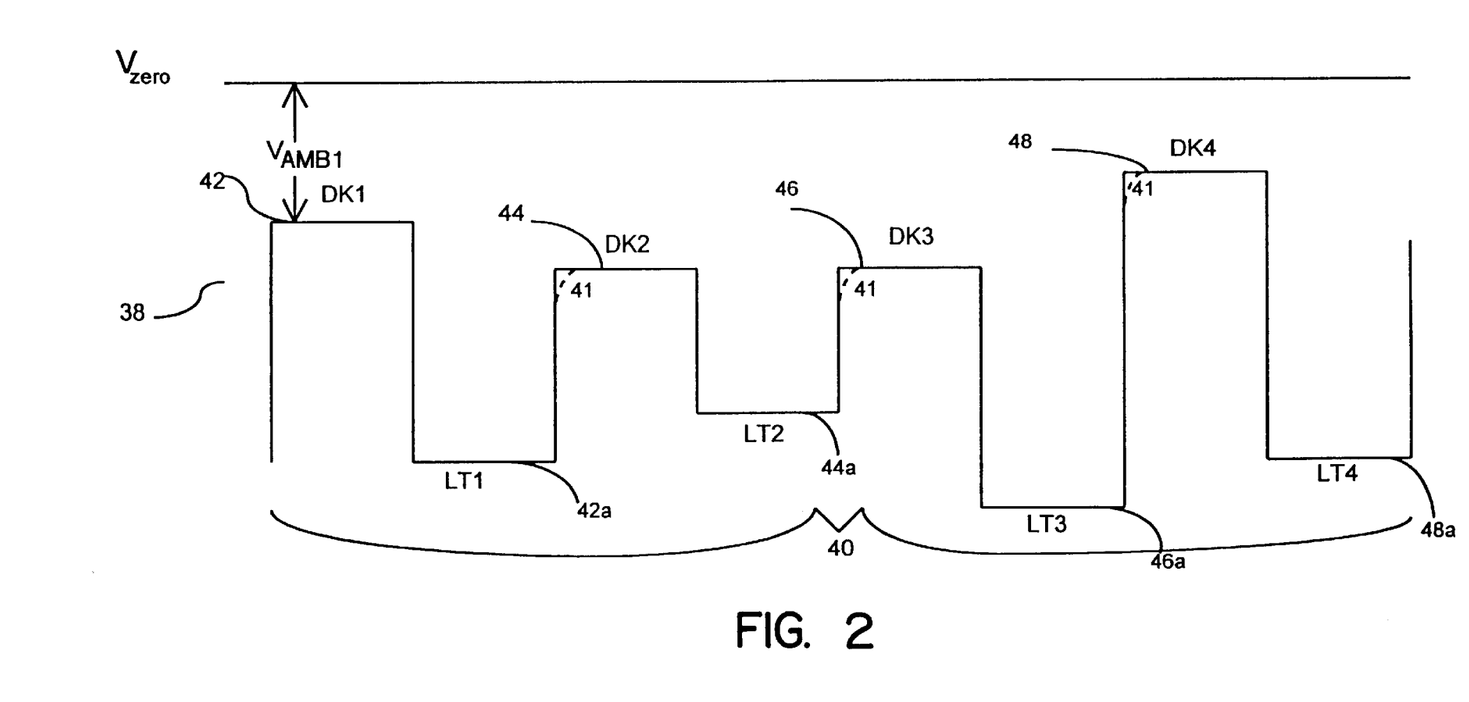
FIG. 2 is a waveform illustrating a TDM signal produced at the preamplifier output by the system of the present invention.

Referring to FIG. 2 the TDM signal 38 includes a series of pulse groups 40 output by the photodiode 26 in response to the detection of light passed through finger 24. Each pulse group includes, in this case, a negative going "light 1" (hereinafter "LT1") portion, or interval, and a negative going "light 2" (hereinafter "LT2") portion, or interval, and in the case of four emitters, a negative going "light 3"(hereinafter "LT3") portion, or interval, and a negative going "light 4" (hereinafter "LT4") portion, or interval corresponding to the detected levels of light at each of the emitted and transmitted wavelengths. Ambient light is also detected by photodiode 26 together with the detected light corresponding with the light beam 16 at the first wavelength, the light beam 17 of the second wavelength, the light beam 18 of the third wavelength and the light beam 19 of the fourth wavelength. This ambient light is manifested within the output signal of the photodiode 26 as an offset voltage. That is, the LT1, LT2, LT3 and LT4 signal portions (42a, 44a, 46a and 48a, respectively) each include an offset which results from ambient light that is incident upon the photodiode 26 during the time that the LT1, LT2, LT3 and LT4 signal portions (42a, 44a, 46a and 48a, respectively) are generated by the four emitters 20, 21, 22 and 23. In order to facilitate removal of the offset, TDM signal 38 includes a "dark 1" (hereinafter "DK1") portion, or interval 42, inunediately preceding LT1, and a "dark 2" hereinafter "DK2") portion, or interval 44, immediately preceding LT2 and in the case of four emitters a "dark 3" (hereinafter "DK3") portion, or interval 46, immediately preceding LT3 and a "dark 4" (hereinafter "DK4") portion, or interval 48, immediately preceding LT4. The voltage level during each of the DK1 and DK2 (and in the four emitter case, DK3 and DK4) intervals represents the ambient light level incident upon photodiode 26 in the absence of transmitted light from any one of the four emitters 20, 21, 22 and 23. . The voltage levels of DK1, DK2, DK3 and DK4 are also dependent upon the gain set for the switched gain preamplifier 54. For example, in FIG. 2, DK2 and DK3 are substantially equivalent because the gain set for these two signal portions is the same, however, the gain for signal portions DK1 and DK4 are different from each other and from the gain for signal portions DK2 and DK3.

The difference in voltage between $V_{zero}$ and DK1 $V_{ambl}$, represents the 1 ambient light offset present in TDM signal 38 amplified according to the gain set for signal portion 42. Such an ambient light level may result from any light source including, for example, room lighting or sunlight. As will be appreciated, subtraction of the "dark time" portions DK1, DK2, DK3 and DK4 voltages from the LT1 LT2, LT3 and LT4 portions, respectively, will result in elimination of the ambient light data from the signal of interest, i.e., data corresponding with the transmitted light from light beams 16, 17 18 and 19 which has passed through finger 24. It should also be appreciated that an offset created by ambient light may produce a DC offset as illustrated in FIG. 2 or it may produce some AC offset.

The problem encountered with the measurement of the ambient light level following a period of excitation of the photodiode by an emitter is that the signal from the photodiode 26 does not decay instantaneously as depicted in the solid line in TDM signal 38 of FIG. 2. Rather, depending on the characteristics of the photodiode the amount of time the signal from the photodiode 26 representative of its excitation by the previous emitter (e.g., LT1) may take several hundred microseconds to decay from 10% of the maximum value to 0.1% of the maximum value for that excitation. This phenomenon is referred to as "bleed-through". Voltage which is actually indicative of the excitation of the photodiode 26 is "bleeding through"into the period which should be indicative only of the dark time or ambient light level. If the decay of the photodiode were instantaneous, the measurement of the "dark time" voltage would be correct, however, due to device characteristics the decay time is not instantaneous and the TDM signal at the transition of light time to dark time is more like dotted line portions 41 or possibly even greater.

Thus, a capacitor which later integrates the voltage representing the dark time for each channel, for instance the DK2 portion of TDM signal 38, will include some of the (negative) voltage from LT1 which is bleeding through into DK2. This "bleed-through" may not be particularly bothersome when channel 1 and channel 2 have identical preamplifier gains. However, if in the switched-gain amplifier the gain of channel 1 is set at "zero" (for instance at 10 K Ohm) and LT1 is approximately 2V and the gain of channel 2 is set near the maximum of 8 then during the first microseconds after turning off the first emitter the preamplifier will attempt to multiply the 2V by the ratio of the actual gain of channel 2 to the actual gain of channel 1—a possible ratio of about 140. Under these conditions the pre-amplifier output would temporarily saturate between approximately 3.2 V and 4.0 V (depending on the specific characteristics of the operational amplifier) and could require dozens of microseconds to come out of saturation and an additional similar period of time to decay. The voltage which bleeds through is thus amplified and becomes an erroneous portion of the integrated DK2 which then becomes an erroneous offset to LT2 when DK2 is subtracted from LT2.

Figure 3:
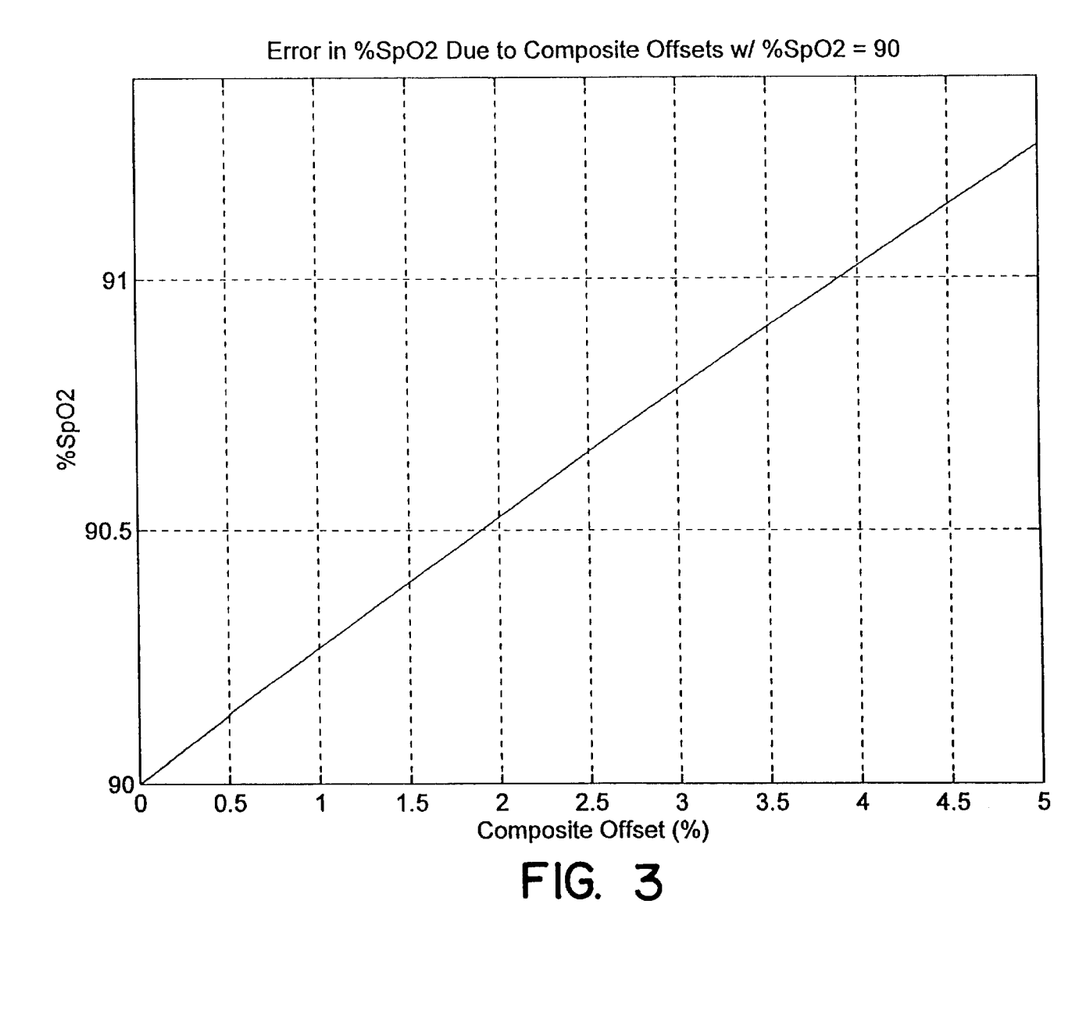
FIG. 3 is a graph depicting the error in the calculation of oxygen saturation due to composite offsets.

FIG. 3 shows the estimated effect of this bleed-through on the calculation of saturation (SpO2).

The following Table 2 shows experimental data for one particular silicon photodiode which provides an idea of the number of mV which will erroneously appear as part of the integrated DK2 value due to the "bleed-through" effect. A laser diode having a spectral content centered around the nominal wavelength of 980 nm was used.

TABLE 2

| GAIN SETTING CHANNEL 1 | GAIN SETTING CHANNEL 2 | "Bleed-Through" Offset (mV) |
|---|---|---|
| X<br>X = 0 or 1 | X to X + 5<br>X + 6 | <1<br><2 |
| 2 | 8 | <4 |
| 0 | 7 | <7 |
| 1 | 8 | <13 |
| 0 | 8 | <86 |

The following Table 3 shows how the effect of "bleed-through" varies for the particular silicon photodiode with the change in the center (nominal) wavelength of the emitter.

TABLE 3

| NOMINAL WAVELENGTH (nm) | "Bleed-Through" OFFSET (mV) |
|---|---|
| 635 | 1.0–1.5 |
| 670 | 1.0–1.5 |
| 810 | 2 |
| 905 | 4 |
| 955 | 8–10 |
| 980 | 8–10 |

Tables 2 and 3 show the "bleed-through" effect caused by photodiodes which have a slow rate of decay. The rate of decay for these "slow-turnoff" photodiodes is the cause of error. It is not possible to determine the rate of decay of a photodiode by a visual inspection. Silicon photodiodes which are commercially available in quantities sufficient for photoplethysmographic sensors and at a price low enough to make such sensors commercially acceptable vary substantially in decay time. Therefore, in order to implement the photoplethysmographic instruments with fast-turnoff photodiodes of the present invention it is necessary to screen photodiodes (or at least a sampling of the photodiodes) at some point in the manufacturing process which have an unacceptable decay time from the fast-turnoff photodiodes having an acceptable decay time.

Figure 4:
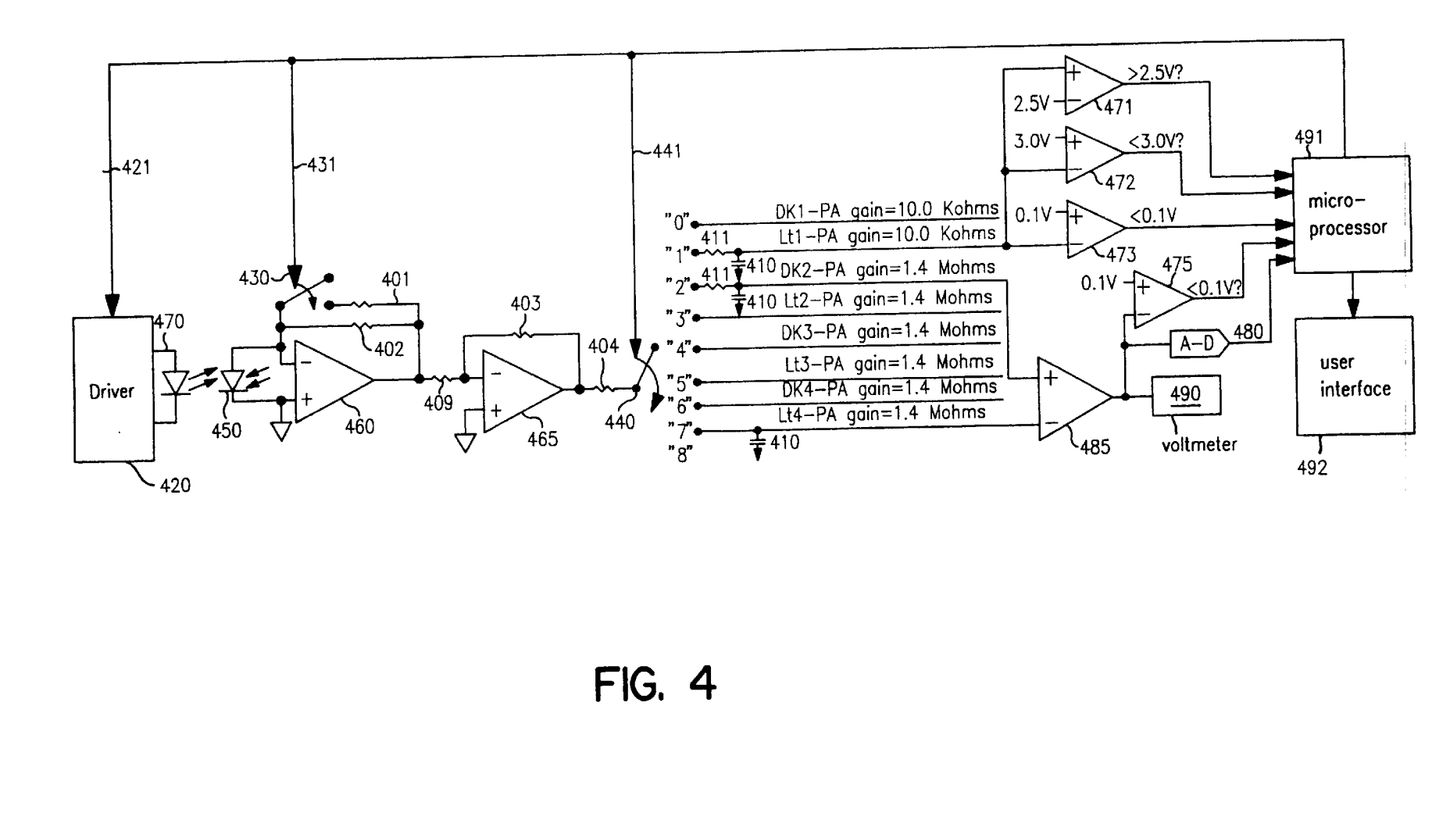
FIG. 4 is a block diagram illustrating the components of an embodiment of a hardware test unit for detecting fast-turnoff photodiodes.

Two methods of detecting the fast-turnoff photodiodes are disclosed below: one implemented in hardware and the other in software internal to the photoplethysmographic instrument. FIG. 4 depicts the hardware required to provide a testing apparatus for testing the commercially available photodiodes in order to select the fast-turnoff photodiodes from the universe of photodiodes. Test photodiode 450 is placed between the terminals of operational amplifier 460. Resistor 401, which is preferably 10.0 K Ohm is selected via switch 430 which is preferably a processor controlled silicon switch (two pole). In combination with resistor 402 which is preferably 1.4 M Ohm the gain of the test circuit of FIG. 4 can be selected using solid state switch 430. The second operational amplifier 465 and resistors 403 and 409, preferably having resistances of 10.0 K Ohm and 100 Ohm respectively, provide inversion of the voltage signal. Resistor 404, preferably having resistance of 100 Ohm, in combination with capacitors 410 provides additional filtering. Silicon switch 440 permits the demultiplexing of the TDM signal received from photodiode 450 through the preamplifier circuit. Capacitors 410, preferably 1.0 µF and resistors 411, preferably 2 K Ohm, provide for the low-pass filtering and integration of the demultiplexed signal portions DK1, LT1, DK2, LT2 and LT4. The LT1 signal portion output of the low-pass filter and hold circuit of 410 and 411 is compared to three different voltage levels using comparators 471, 472 and 473 in order to determine whether output of the emitter 470, i.e., LT1 falls within the range of 2.5 to 3.0 V at a given gain. It is important for testing purposes that the emitter 470 be driven into a predetermined range such as 2.5 to 3.0 V. Comparator 475 is used to compare the bleed-through on DK2 after amplification by instrumentation amplifier 485 having a gain set to 100. The value of the bleed-through voltage is also sent to an analog-to-digital converter 480 and to a digital voltmeter 490 in order to inform the user of the actual bleed-through voltage value. The output of the comparators and the analog-to-digital converter is then sent to programmable logic device or microprocessor 491, either in a personal computer or embedded in the test unit for generation of the user display messages described below in reference to FIG. 6. Messages are then displayed via a user interface 492 such as a personal computer monitor or LED's which notify the user of a select set of predetermined messages.

Figure 5:
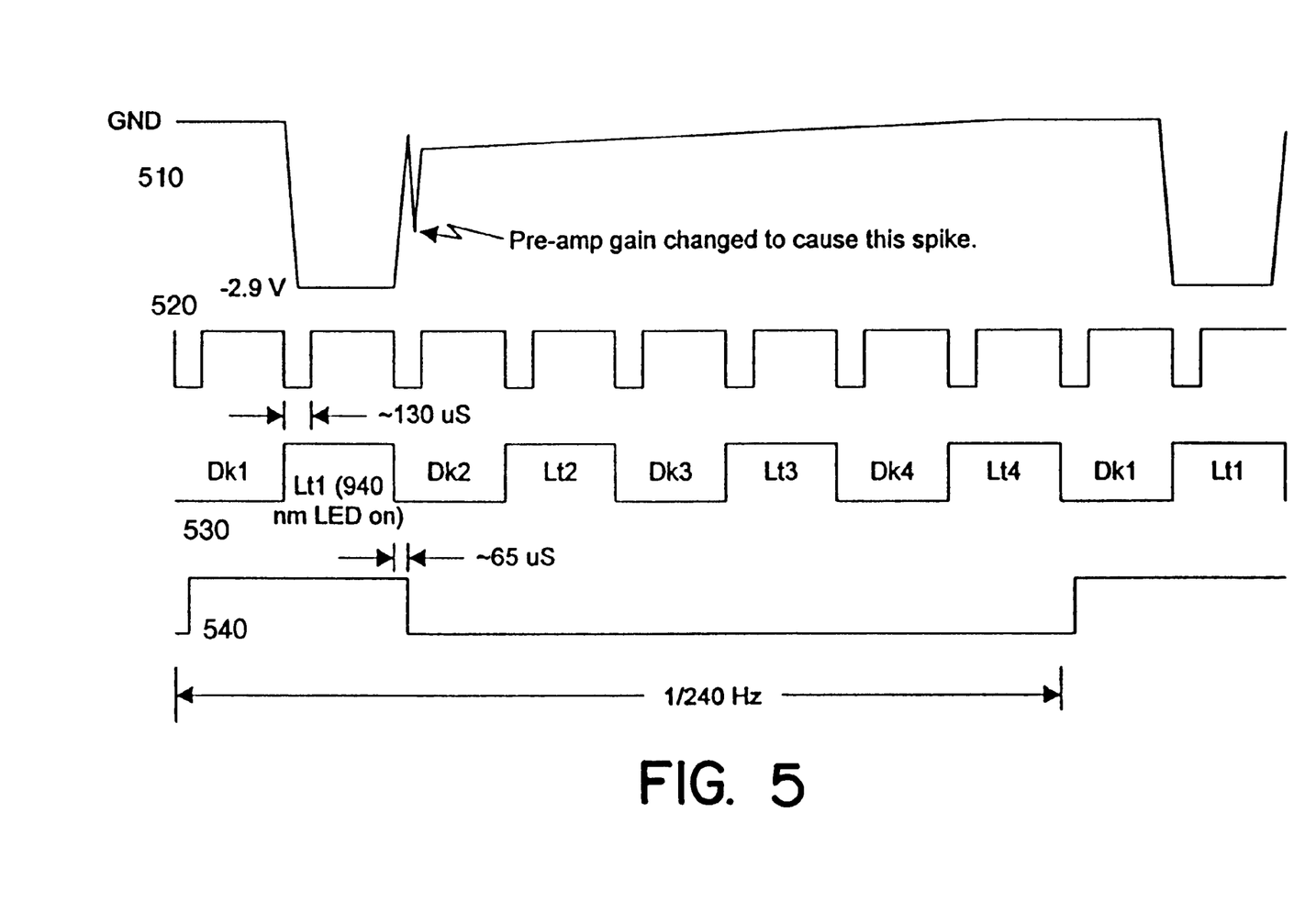
FIG. 5 is a diagram of the timing and associated output of the preamplifier section of the hardware test unit of FIG. 4.

Emitter 470 is preferably approximately 900–985 nm and is used to excite the test photodiode 450 to generate the LT1 portion of the signal. Emitter 470 is driven by driver 420. Driver 420 and silicon switches 430 and 440 are controlled via control lines 421, 431 and 441 by programmable logic device or microprocessor 491 according to the control timing diagram of FIG. 5. Signal 510 depicts the output of the pre-amplifier negative going from the first operational amplifier 460. Signal 520 depicts the timing of the enablement of the -multiplexer switch 440 for charging of the capacitors 410. Signal 530 depicts the timing of the turning on and off of the four light emitters although in the test circuit only one emitter 470 is used to emit light corresponding to signal portion LT1. Signal 540 depicts the timing of the input to switch 430 which is in the high state only for channel one (LT1) and then switches to the low state approximately 65 microseconds after the turn off of the emitter 470.

Figure 6:
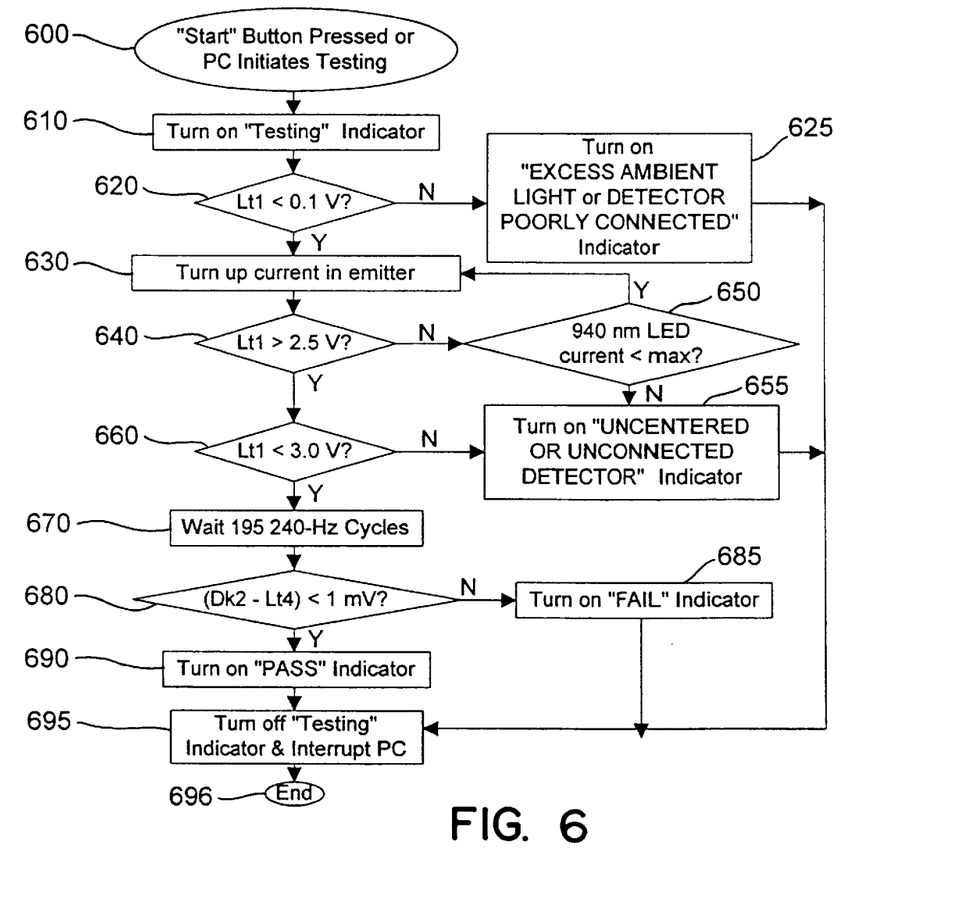
FIG. 6 is a flow diagram of the operation and logic associated with the hardware test unit of FIG. 4.

Use of the test circuit of FIG. 4 and the method of testing can be seen in the flow diagram in FIG. 6. Fast-turnoff photodiodes are identified by comparing the integrated voltage at DK2 to the integrated voltage of LT4 (considering controlled ambient light). After depression of the start button 600 on the test unit or the initiation of the test through the control of a personal computer a "Testing" message is displayed 610 or the "Testing" LED is illuminated on user interface 492. The voltage of LT1 is then compared in step 620 to an ambient threshold level of 0.1 V. If the ambient level on LT1 prior to driving emitter 470 at all exceeds the 0.1 V threshold then the "EXCESS AMBIENT LIGHT OR DETECTOR POORLY CONNECTED" indicator is illuminated or displayed in step 625. If the ambient light level on LT1 is below the 0.1 V threshold then the driver 420 is used to drive the emitter 470 in step 630. LT1 is again checked in steps 640 and 660 in order to set the output of LT1 to between 2.5 V and 3.0 V. If this range cannot be reached before the emitter 470 is being driven by driver 420 at its maximum current then step 655 displays an error message "UNCENTERED OR UNCONNECTED DETECTOR." After waiting 195 240 Hz cycles (an arbitrary value to allow capacitors 410 to charge) in step 670 LT4 is subtracted from DK2 and the result is compared to the 1 mV threshold in step 680 via comparator 475. It should be appreciated that both the number of cycles and the threshold value may need to be varied for different types of photodiodes and photoplethysmographic systems. If the result of the subtraction of LT4 from the voltage seen on DK2 is less than the 1 mV or other determined threshold then the "PASS" indicator is illuminated or displayed in 690 otherwise the "FAIL" indicator is illuminated or displayed in step 685. After completion of the test the "TESTING" indicator is turned off in step 695 and the test is ended.

Figure 7:
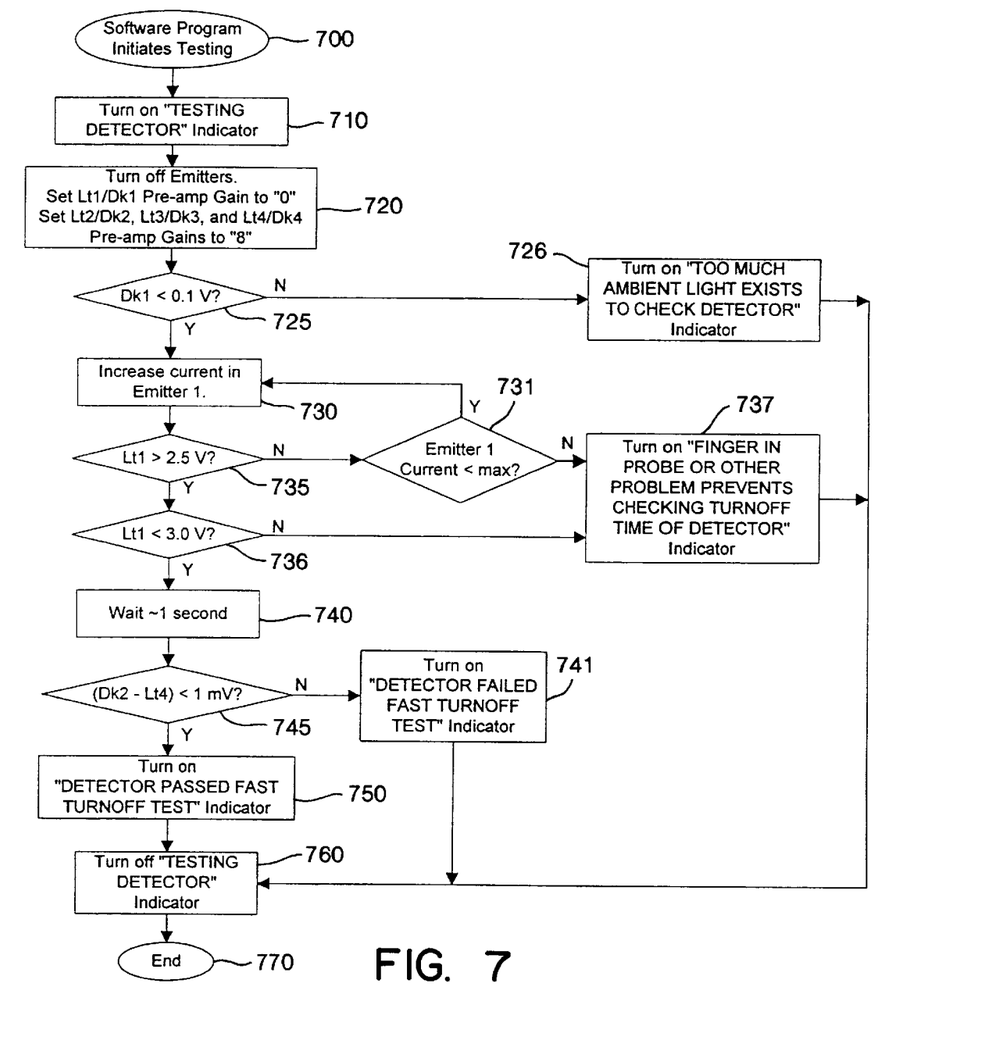
FIG. 7 is a flow diagram depicting a software implemented test for detecting fast-turnoff photodiodes in the photoplethysmographic system of FIGS. 1, 1babd 1c.

The software implementation of the flow diagram of FIG. 7 implements the test in a real-time software routine. The first step 710 in the software routine is to illuminate or display a "Testing Detector" indicator. In the second step 720 the emitters are turned off and the preamplifier gain levels for DK1 and LT1 are set to zero while the preamplifier gains for LT2, DK2, LT3, DK3, LT4 and DK4 are set to "8" on preamplifier 54. The third step 725 is a comparison of the voltage representing DK1 to an ambient threshold level of 0.1 V. If the ambient level on DK1 prior to driving or exciting an emitter 20, 21, 22 or 23 exceeds the 0.1 V threshold then the "EXCESS AMBIENT LIGHT OR DETECTOR POORLY CONNECTED" indicator is illuminated or displayed in step 726. If the ambient light level on DK1 is below the 0.1 V threshold then the emitter driver section 52 is used to drive the first emitter 20. LT1 is again checked in steps 735 and 736 in order to set the output of LT1 to between 2.5 V and 3.0 V. If this range cannot be reached before the first emitter 20 is being driven by emitter driver section 52 at its maximum current detected in step 731 then step 737 displays an error message "FINGER IN PROBE OR OTHER PROBLEM PREVENTS CHECKING TURNOFF TME OF DETECTOR," After an approximately one second delay in step 740 (an arbitrary value to allow capacitors to charge) LT4 is subtracted from DK2 and the result is compared to the 1 mV threshold in step 745. If the result of DK2–LT4 is greater than 1 mV at the above settings and emitter wavelengths then the photodiode should not be used with a photoplethysmographic device which uses switched gain preamplification and the test result "DETECTOR FAILED FAST TURNOFF TEST" is displayed in step 741. If the variation is less than 1 mV, or some other threshold level considered significant, then the result in step 750 that the "DETECTOR PASSED FAST TURNOFF TEST" is displayed or illuminated. The acceptable threshold in step 745 will vary with the type of detector and the photoplethysmographic monitor. In steps 760 and 770 the "Testing Detector" indicator is turned-off and the test is ended.

It can be seen that to apply the above invention to the various photoplethysmographic measurement instruments which can be developed a wide variety of emitter wavelengths, circuitry and test apparatuses can be used. Therefore, the described embodiment is to be considered as illustrative and not restrictive, and the invention is not to be limited to the details given herein.

I claim:

1. A photoplethysmographic measurement system for use in determining a value for at least one blood analyte level comprising:

an emitter which emits a plurality of light beams through a portion of said tissue wherein each of said light beams is transmitted through said tissue for a discrete time interval and wherein each of said light beams has a distinct spectral content characterized by a center wavelength;

a fast response detector which generates a time-division multiplexed signal indicative of light transmitted through said tissue wherein said signal has a first signal portion indicative of the light transmitted by a first light beam of said plurality of light beams and a second signal portion indicative of said ambient light level a preamplifier wherein said first signal portion and said second signal portion may be amplified at substantially different gains wherein said fast response detector is selected so as to minimize the effect of the first signal portion on the second signal portion when said second signal portion is amplified at a substantially greater gain than said first signal portion; and a microprocessor wherein a computer program is executed which contains a test routine to determine whether the detector has an acceptable decay time.

2. The photoplethysmographic measurement system of claim 1 further comprising a demultiplexer which separates said first and second signal portions and wherein the preamplifier is a switched-gain preamplifier which amplifies said first and second signal prior to separation by the demultiplexer.

3. The improved photoplethysmographic measurement system of claim 2 further comprising an integrator which integrates the value of said first and second signal portions for each discrete time interval for providing a total first light level and a total first ambient light level.

4. The photoplethysmographic system of claim 3, wherein said computer program controls the plurality of emitters, the preamplification means, the demultiplexer and the integrator and said test routine controls the excitation of one of the plurality of emitters, the gain of the preamplifier, generates a third signal portion indicative of the ambient light level prior to said first signal portion for a discrete time interval and compares said third signal portion with said second signal portion so as to determine whether the detector has said acceptable decay time.

5. A photoplethysmographic measurement system for use in determining a value for at least one blood analyte in a patient's tissue using a time division multiplexed signal in an environment including ambient light, said system comprising:

emitter means for emitting a plurality of light beams through a portion of said tissue wherein each of said light beams is transmitted through said tissue for a discrete time interval and wherein each of said light beams has a distinct spectral content characterized by a center wavelength;

fast response detector means for generating a signal indicative of light transmitted through said tissue wherein said signal has a first signal portion indicative of the light transmitted by a first light beam of said plurality of light beams and a second signal portion indicative of said ambient light for a discrete time interval said fast response detector means having a decay rate characteristic; relating to a response speed upon deactivation of said light, of at least a predetermined value for certain operating parameters;

switched gain preamplification means wherein said first signal portion and said second signal portion may be amplified at substantially different gains, said substantially different gains being reflected in said operating parameters;

an integrator for measuring the total voltage associated with said first signal portion and said second signal portion for each said discrete time interval;

wherein said fast response detector means is selected so as to minimize the effect of the switched gain preamplification of said first signal portion of the integrated voltage associated with said second signal portion; and a microprocessor wherein a computer program is executed which controls the plurality of emitters, the preamplification means, and the integrator and which contains a test routine which controls the excitation of one of the plurality of emitters, the gain of the preamplification means, further generates a third signal portion indicative of the ambient light level prior to said first signal portion for a discrete time interval and compares said third signal portion with said second signal portion so as to determine whether the detector has an acceptable decay time.

6. The improved photoplethysmographic measurement instrument of claim 5 wherein the detector is a photodiode.

7. The improved photoplethysmographic measurement instrument of claim 5 wherein the detector is a silicon photodiode.

* * * * *